US005911709A

United States Patent [19]

Hogan

[11] Patent Number: 5,911,709

[45] Date of Patent: Jun. 15, 1999

[54] VACCINE PACK

[76] Inventor: Thomas Hogan, 2420 Westport Cir., Marietta, Ga. 30064

[21] Appl. No.: 08/579,258

[22] Filed: Dec. 27, 1995

[51] Int. Cl.[6] .............................. A61M 5/00

[52] U.S. Cl. .............................. 604/232; 222/529; 206/363

[58] Field of Search .............................. 604/191, 192, 604/232, 181, 187; 128/919; 206/363, 370, 570, 571; 224/223, 674, 675, 679, 901.8, 148.2, 148.7; 222/93, 95, 527, 529, 530

[56] References Cited

U.S. PATENT DOCUMENTS

| | | | |
|---|---|---|---|
| D. 324,819 | 3/1992 | Eisenberg . | |
| 5,135,144 | 8/1992 | Blakely . | |
| 5,154,324 | 10/1992 | Stratford | 222/175 |
| 5,171,214 | 12/1992 | Kobler | 604/82 |
| 5,380,296 | 1/1995 | Semedley | 604/193 |
| 5,533,618 | 7/1996 | Pickels, Jr. | 206/363 |

*Primary Examiner*—Michael Powell Buiz
*Assistant Examiner*—At Nguyen
*Attorney, Agent, or Firm*—Troutman Sanders, LLP

[57] ABSTRACT

The present invention relates to an vaccine pack (10) which comprises an insulated container (12) having an automatic syringe (18) and a plurality of needle holders (20) attached thereto. A strap (14) having a strap first fastener (14A) is securely attached at one distal end to the container (12). A strap second fastener (14B) is securely fastened to the the container (12) such that the strap (14) can loop around an over a member and removably attach to the strap second fastener (14B) thereby positioning the vaccine pack (10) underneath the member away from direct sunlight.

9 Claims, 3 Drawing Sheets

VACCINE PACK

BACKGROUND OF THE INVENTION

1. Field of the Invention

The present invention relates to vaccine pack. More particularly, the present invention relates to vaccine pack which contains and maintains vaccines at a constant temperature and also is capable of holding needles as well as an automatic syringe.

2. Description of the Prior Art

Prior art inventions mostly comprise inventions to store medicine and/or vaccines. However, none deal with the problem of field use for vaccinating animals. In the field there are considerable environmental and physical conditions which must be addressed in designing a delivery system The environmental conditions which may effect vaccine effectiveness are sunlight and temperature. Physical conditions which must be addressed are being lightweight for transportation, ruggedness, compactness and ease of use. The prior art inventions do not address all the environmental and physical conditions that an animal vaccination system must address to be used in the field.

Numerous innovations for medicine containers have been provided in the prior art that are described as follows. Even though these innovations may be suitable for the specific individual purposes to which they address, they differ from the present invention as hereinafter contrasted.

In U.S. Pat. No. 5,171,214, dated, Dec. 15, 1992, titled, Named Drug Storage and Delivery System, invented by Kolber et al.,comprises a drug storage and delivery system that includes a drug containing vial assembly, a syringe assembly, and an adapter assembly for attaching the vial assembly to the adapter assembly. The vial assembly includes a vial that is provided with a pierceable stopper and a skirt member that circumscribes the outside of the vial. The syringe assembly includes a cannula extending longitudinally therethrough. The adapter assembly attaches the vial assembly to the syringe assembly in a manner that permits communication between the interior of the vial and the cannula extending through the syringe. The system also permits attachment of the syringe assembly to a container filled with a diluent and means for delivering the diluent into the vial assembly and subsequently directing the mixed solution back into the container.

The present invention differs from the above described invention because the patented invention is inconvenient to use and much more complicated in its part system. In addition the patented invention is not applicable to the livestock industry because it is not rugged enough in design. Furthermore, the patented invention is much more complicated to manufacture and sell again leaving it less applicable to the low margin livestock industry. The patented invention is not designed to compliment the livestock industry's widely used automatic dosage syringes as the present invention is designed to do. The patented invention is similar in application in that it stores and distributes a drug from a vial. U.S. Pat. No. 5,171,214 is greatly dissimilar in convenience of application being much more abstract and complicated. It is therefore not applicable to the beef or livestock industry as there are too many parts. Being a more complicated device it would also be more expensive to manufacture and sell again leaving it less applicable to the low margin livestock industry. This is a multiple mechanism device (three assemblies), not a simple singular device like the Vac-Pac. It is not designed to compliment the livestock industries widely used automatic dose syringes. Its' dispensary end will not accept the supply end of these syringes. Changing drug vials is not nearly as convenient with U.S. Pat. No. 5,171,214 as with my Vac-Pac. There is no needle storage area or mechanism on this device as there is on the Vac-Pac. Once again decreasing convenience and application efficiency. U.S. Pat. No. 5,171,214 has no means by which to attach it to a person or livestock restraint mechanism during livestock processing, as does the Vac-Pac. U.S. Pat. No. 5,171,214 has no area for convenient storage of an automatic dose syringe, presently used in the livestock industry. The materials of construction are completely different. The Vac-Pac has no adapter assembly for diluting the vaccine as does this device. This device is solely applicable to human health whereas the Vac-Pac will strictly be used by the animal health industry.

In U.S. Pat. No. 5,135,144, dated, Aug. 4, 1992, titled, Insulated Drug Supply Pouch Storage, invented by Blakely et al, comprises a belt worn and readily portable medical supply pouch for holding a supply of drug containers in a temperature stable and contamination resistant environment is disclosed. A substantially rectangular housing fabricated from a thick insulating material comprising a bottom, two side panels, a front and a back panel with an open top. The housing thus formed defines a cavity therein for storing a supply of drug cartridges. A protective panel extending across the opening of the housing and angled downward into the cavity is provided to prevent contamination from entering the cavity, while providing access by the hand of a user through the opening and down into the cavity for retrieving one of the drug containers. The housing is covered inside and out by a water-proof and contamination-resistant nylon material. Two belt loop members are affixed to the back panel of the housing for attaching the pouch to the waist belt of a user. An internal pocket inside the cavity of the housing is provided for containing a heating element for heating the interior cavity. An outside auxiliary pocket is attached to the outside surface of the front panel for storing items not requiring an insulated and contamination free environment.

The above described patented invention differs from the present invention because this device is designed to store numerous small vaccine vials for removal dispensing of drug, then return to storage (20). The vaccine pack is intended to hold one multi-dose vial for direct dispensary of the drug. In addition, the patented invention has no means by which to administer the drug directly from within, it is only intended to store vials and small single dose syringes (20). Furthermore, the patented invention has no provision for direct attachment of a multi-dose automatic syringe has been made on this device. The insulated drug supply pouch has no provisions for attachment to a livestock restraining device. It has a singular focus of attachment to a belt on a person. U.S. Pat. No. 5,135,144 has provision for the storage and use of a heating device (21) which is not applicable or necessary with the vaccine pack as it holds the vial closely within full insulation.

In U.S. Pat. No. Des. 324,819, dated, Mar. 24, 1992, titled, Portable Dispensing Case for Medication, invented by Eisenberg, comprises the ornamental design for a portable dispensing case for medication, as shown and described.

The above described patented invention differs from the present invention because the patented device is designed for the storage and dispensary of single doses of medication in the solid form (pills) and not the storage and dispensary of a liquid drug in a vial. This device has no application to the livestock industry. It can not be attached to a livestock restraint device. U.S. Pat. No. 324,819 has no provisions for the storage and use therefrom of needles or an automatic dose syringe. Furthermore, there is no temperature insulation in the patented invention nor provisions for attachment of an automatic dose syringe. The patented invention is not intended for multiple patient or recipient application of a drug.

In U.S. Pat. No. 5,380,296, dated, Jan. 10, 1995, titled, Multi-Celled Safety Package, Needle Guard and Safe Disposal Module for Pre-Filled Medication Cartridges, invented by Smedley et al, comprises a self-packaging safety syringe set (2) uses a unitary molded set of enclosure units (8,104) sized for housing conventional cartridge-needle units (12) therein. The set of enclosure units are connected to one another by frangible connections (64,66,130,138). The cartridge-needle unit has a hollow barrel (14) with a needle assembly (24) mounted to one end and a piston (16) mounted therein. Each enclosure unit includes a body section (38,106), a stem section (44,108) is broken to remove the stem section to expose the needle (26) for use. The removed stem section is used to drive the piston within the barrel. After use, the barrel is pulled back through the body section so that the needle is completely housed within the body section. At that point radially inwardly extending spring fingers (84,132) engage a shoulder (76) on the hub (34) of the needle assembly to keep the needle assembly from being withdrawn from the body section to permit a safe disposal of the used syringe. The syringe set needs no special packaging and no holders for the cartridge-needle units, the enclosure units serving as both.

The present invention differs from the above described patented invention because this device is for the storage of a single dose syringe. It provides no means by which to store and dispense from a multiple dose drug vial. U.S. Pat. No. 5,380,296 does not provide for dispensing the drug directly from this apparatus. Has no provisions for attachment to livestock handling or restraining device. Does not have a location for storage of extra needles. Does not provide insulation for drug from drastic temperature changes.

Numerous innovations for vaccine packs have been provided in the prior art that are adapted to be used. Even though these innovations may be suitable for the specific individual purposes to which they address, they would not be suitable for the purposes of the present invention as heretofore described.

SUMMARY OF THE INVENTION

The vaccine pack will be used to hold and insulate animal vaccine bottles during normal farm animal medical processing. It will also hold extra needles, as these must be replaced periodically (every 25–50 animals) during a normal animal processing period. In addition the vaccine pack has a Velcro side (male) where an automatic syringe, equipped with a VELCRO (TM) sock (female) may be attached for easy access & safe keeping. The strap which holds the vaccine pack in place will provide a location for a VELCRO (TM) label used to identify the vaccine being held inside.

Product Advantages

1. Quality Control:

1a. Maintains vaccine at a constant temperature. Fluctuations in vaccine temperature can cause damage to the vaccine itself, decreasing its' effectiveness and increasing the chance for meat contamination.

1b. Will not allow vaccine to be exposed to direct sunlight, which can also cause damage to the vaccine.

1c. Easy access to the held in place, fresh clean needles will provide for regular needle changes. Clean, sanitary needles will help to decrease the amount of vaccine blemishes in the meat of the animal.

1d. An out of the way, out of the dirt, storage position for the automatic syringe will improve sanitary vaccine application conditions.

1e. Interchangeable VELCRO (™) labels on the outside of the vaccine pack will, at a glance, keep the operator informed of the type and quantity of vaccine being administered, reducing the chances of improper, or unwanted vaccine application.

1f. The overall simplicity of construction materials in the vaccine pack provide for easy cleaning and sanitation with soap and water.

2. Safety:

2a. The foam rubber construction provides for the safe keeping of vaccines, which are often contained in glass bottles. The vaccine pack will protect the glass vile and decrease the chances of its being inadvertently broken, which would endanger both the animal and the operator.

2b. Isolation of replacement needles will prevent needles from being haphazardly stored or tossed around, decreasing the chances of needles being misplaced and possibly consumed by an animal or stepped on by the operator.

2c. Providing a constant location for the automatic syringe decreases the chance that an operator or an animal might accidentally come in contact with the needle, step on the syringe or get tangled up in the hose.

3. Application Efficiencies:

3a. The VELCRO (™) strap and foam rubber construction will allow for quick removal and a quick change or replacement of the vaccine container.

3b. Replacement needle storage will reduce time and effort required in changing out needles on the automatic syringe. Reducing processing time and operator fatigue.

3c. Quick and easy removal and placement of the automatic syringe increases vaccine application efficiency and reduces operator fatigue.

3d. The outside vaccine label serves as a constant reminder of type and quantity to be used, reducing product waste.

3e. The vaccine pack can also be used in the field as it could easily be attached to the operators belt or to the saddle in the case of in-pasture cattle care. In regards to this, all of the same safety and efficiency features will still apply.

In summary, the vaccine pack has across the board application to all segments of the animal production industry. It provides improved quality control for both product of application and the product being developed, in this case meat for human consumption. The vaccine pack vastly improves safety for both the animal being treated and the operator. Increases in production efficiency will be realized immediately upon use of the vaccine pack.

The types of problems encountered in the prior art are vaccines liable to exposures to temperature fluctuations and sunlight exposure.

In the prior art, unsuccessful attempts to solve this problem were attempted namely: medicine packs. However, the problem was solved by the present invention because of insulation and sunlight shielding of the vaccine.

Innovations within the prior art are rapidly being exploited in the subject matter of vaccine administration.

The present invention went contrary to the teaching of the art which describes medicine carriers and packs.

The present invention solved a long felt need to have a lightweight, durable vaccine pack which can be utilized in the field.

The present invention produced unexpected results namely: sunlight exposure was reduced and/or eliminated by the positioning of the strap.

Accordingly, it is an object of the present invention to provide vaccine pack having a strap.

More particularly, it is an object of the present invention to provide a strap having a strap first fastener and strap second fastener.

In keeping with these objects, and with others which will become apparent hereinafter, one feature of the present invention resides, briefly stated, in the vaccine pack having a label to indicate to the user the vaccine type, dosage amount, administration procedures and/or side effects.

When the vaccine pack is designed in accordance with the present invention, automatic syringe has an automatic syringe first fastener an automatic syringe second fastener such that a user can conveniently and rapidly attach the automatic syringe to the vaccine pack to keep it in a safe place while the user manipulates the animal.

In accordance with another feature of the present invention, automatic syringe vaccine inlet has an automatic syringe vaccine inlet through which vaccine enters.

Another feature of the present invention is that the automatic syringe has an automatic syringe vertical handle in a perpendicular configuration to an automatic syringe horizontal handle which increases a user's leverage.

Yet another feature of the present invention is that the automatic syringe has an automatic syringe trigger.

Still another feature of the present invention is that the automatic syringe has an automatic syringe needle fastener.

Yet still another feature of the present invention is that vaccine pack has a plurality of needle holders with corresponding needle holder openings in which extra needles are placed for storage.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawing(s).

BRIEF LIST OF REFERENCE NUMERALS UTILIZED IN THE DRAWING

10—vaccine pack (10)
12—container (12)
12A—container exterior (12A)
12B—container interior (12B)
12C—container top (12C)
12D—container bottom (12D)
12DA—container bottom opening (12DA)
14—strap (14)
14A—strap first fastener (14A)
14B—strap second fastener (14B)
16—label (16)
18—automatic syringe (18)
18AA—automatic syringe first fastener (18AA)
18AB—automatic syringe second fastener (18AB)
18B—automatic syringe vaccine inlet (18B)
18C—automatic syringe hose (18C)
18D—automatic syringe vertical handle (18D)
18E—automatic syringe horizontal handle (18E)
18F—automatic syringe trigger (18F)
18G—automatic syringe needle fastener (18G)

18GA—automatic syringe needle fastener horizontal handle fastener (18GA)
18GB—automatic syringe needle fastener opening (18GB)
20—needle holder (20)
20A—needle holder opening (20A)
22—cattle holder (22)
22A—cattle holder left head member (22A)
22B—cattle holder right head member (22B)
22C—cattle holder top cross member (22C)
22D—cattle holder bottom cross member (22D)
22E—cattle holder right longitudinal member (22E)
22F—cattle holder left longitudinal member (22F)

BRIEF DESCRIPTION OF THE PREFERRED EMBODIMENT

DETAILED DESCRIPTION OF THE PREFERRED EMBODIMENT

Figure 1:
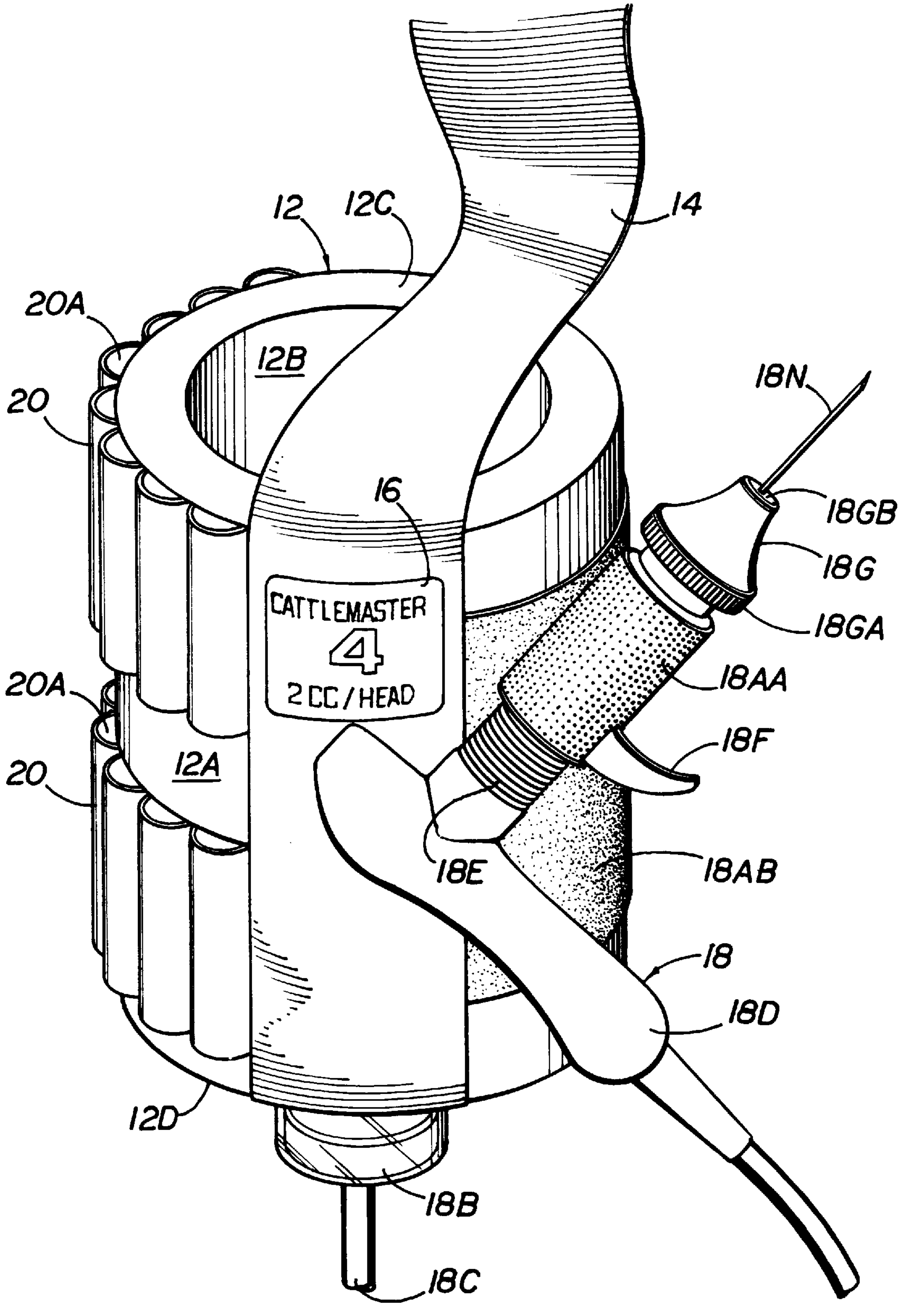
FIG. 1 is a perspective top view of a vaccine pack exhibiting a container having a strap firmly affixed thereon with a automatic syringe attached thereto by a automatic syringe hose.
Figure 2:
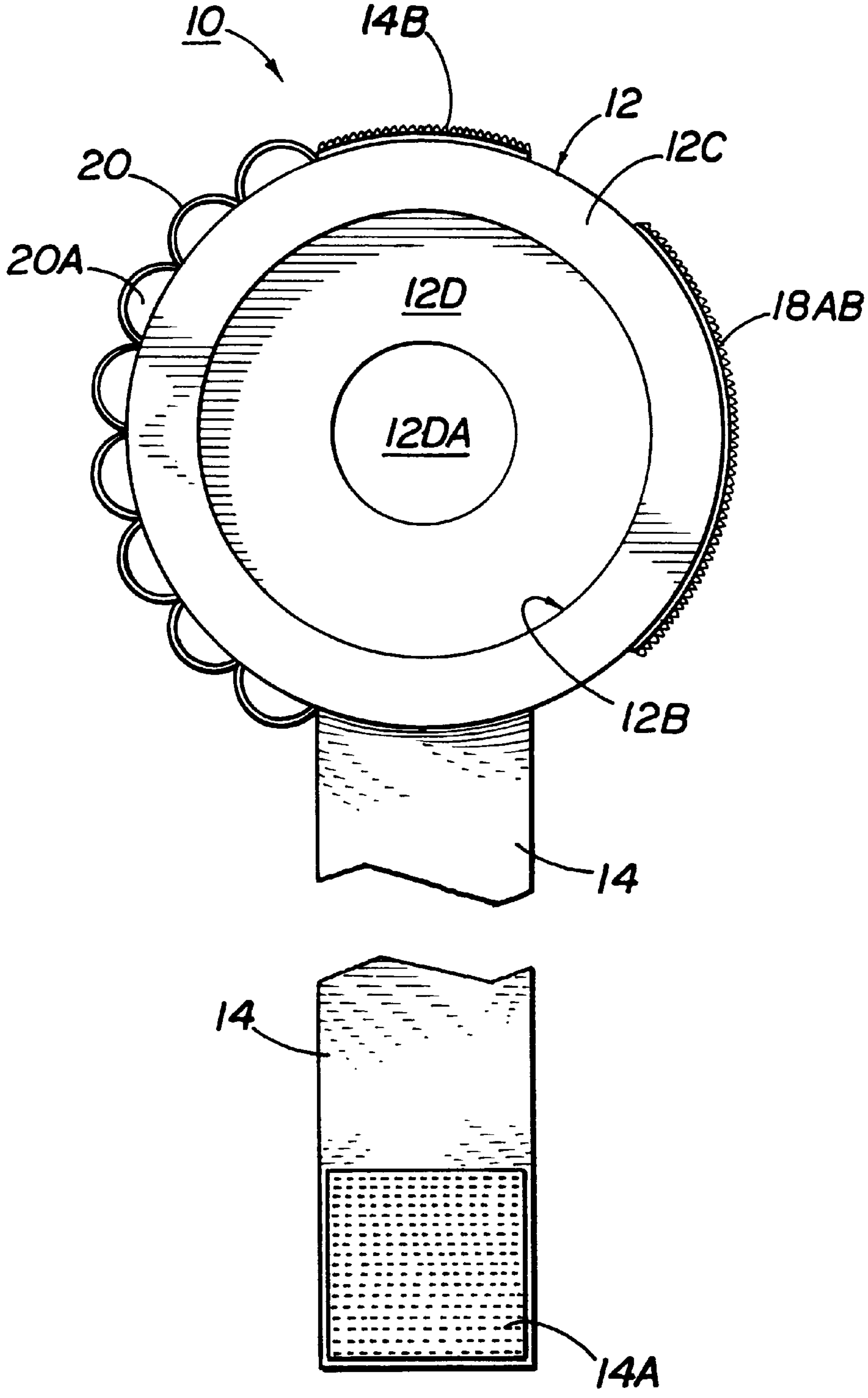
FIG. 2 is a top view of the vaccine pack exhibiting a container having a plurality of needle holders arranged circumferentially and a container bottom opening allowing a automatic syringe vaccine inlet to be inserted therethrough.

FIG. 1 is a perspective top view of a vaccine pack (10) exhibiting container (12) having a strap (14) firmly affixed thereon with a automatic syringe (18) attached thereto by a automatic syringe hose (18C). FIG. 2 is a top view of the vaccine pack (10) exhibiting a container (12) having a plurality of needle holders (20) arranged circumferentially and a container bottom opening (12DA) allowing a automatic syringe vaccine inlet (18B) to be inserted therethrough. The container (12) further comprises a container interior (12B) within which a vaccine bottle is placed in a downward position. The container (12) is constructed from a group of materials consisting of open cell foam, closed cell foam, rubber, rubber composites, plastic, and plastic composites. The container (12) functions to maintain a vaccine at a constant temperature during administration as well as prevent harmful light from reaching the vaccine container. The container (12) further comprises a container exterior (12A) upon which a plurality of needle holders (20) having corresponding needle holder openings (20A) is securely attached thereto. The needle holders (20) are preferably constructed from an elastic type of strap material which is fastened to the container (12) by fastening along vertical seams thereby separating adjacent needle holders (20). The needle holders (20) function to allow the user to place multiple needles in an easily accessible and convenient location on the vaccine pack (10) for use during administration of the vaccine. A new needle must be utilized every 25–50 animals during the vaccination process. The container (12) has a strap (14) securely fastened on one position on the container exterior (12A) preferably in a longitudinal configuration. The strap (14) has a strap first fastener (14A) securely affixed on a distal end. At an opposite position on the container exterior (12A) a strap second fastener (14B) is securely fastened thereto. The strap first fastener (14A) and the strap second fastener (14B) are hook and loop. The strap (14) is utilized to removably attach the vaccine pack (10) to a secure place during the vaccination process. The strap (14) is placed circumferentially around a secure place such as a cattle holder right longitudinal member (22E) and the strap first fastener (14A) is attached to the strap second fastener (14B) having the vaccine pack (10) with the container top (12C) directly underneath the cattle holder right longitudinal member (22E) which further prevents spillage, reduces sunlight exposure and damage to vaccine container during the vaccination process. The strap (14) further comprises a label (16) securely affixed thereon. The label (16) having indicia printed thereon which indicates the type of vaccine being utilized and the dosage amount an well as possibly an administration procedure.

The container (12) has container bottom (12D) which further comprises a container bottom opening (12DA) through which a automatic syringe vaccine inlet (18B) is inserted. The automatic syringe vaccine inlet (18B) has a means by which the vaccine is accessed within the vaccine container. The means is preferably a type of needle means which can be inserted through a rubber top of a vaccine container thereby allowing access to the vaccine itself. Extending from and waterproofly connected at a first distal end to the automatic syringe vaccine inlet (18B) is an automatic syringe hose (18C). At an opposite end of the automatic syringe hose (18C) is an automatic syringe vertical handle (18D) securely and waterproofly connected thereto. The automatic syringe hose (18C) functions to transport vaccine from the vaccine container located in the container (12) to the automatic syringe vertical handle (18D). The automatic syringe vertical handle (18D) has an automatic syringe horizontal handle (18E) integrally attached thereto. The automatic syringe horizontal handle (18E) has an automatic syringe trigger (18F) mounted therein which is connected to a standard check valve (not shown) functioning to administer a predetermined dosage of vaccine to an animal. The automatic syringe horizontal handle (18E) has an automatic syringe needle fastener (18G) attached at a distal end by an automatic syringe needle fastener horizontal handle fastener (18GA) which is approximately a slightly larger diameter than a diameter of the automatic syringe horizontal handle (18E). The automatic syringe needle fastener (18G) further comprises an automatic syringe needle fastener opening (18GB) into which a needle utilized for administering a vaccine to an animal is removably inserted therein. The narrowing of the automatic syringe needle fastener opening (18GB) forms a waterproof connection between the needle and the automatic syringe needle fastener (18G). The automatic syringe horizontal handle (18E) further comprises an automatic syringe first fastener (18AA) which is preferably attached thereon. The automatic syringe first fastener (18AA) could also be placed on the automatic syringe vertical handle (18D). The container exterior (12A) has an automatic syringe second fastener (18AB) securely fastened thereon. The automatic syringe first fastener (18AA) and the complimentary automatic syringe second fastener (18AB) are hook and loop. The automatic syringe first fastener (18AA) on the automatic syringe horizontal handle (18E) allows a user to quickly and conveniently removably attach the automatic syringe horizontal handle (18E) to the container (12) to keep a needle attached to the automatic syringe needle fastener (18G) in a safe place during the vaccination process. Thus a user is able to use both hands to manipulate and position an animal within a cattle holder (22) before and after vaccination.

Figure 3:
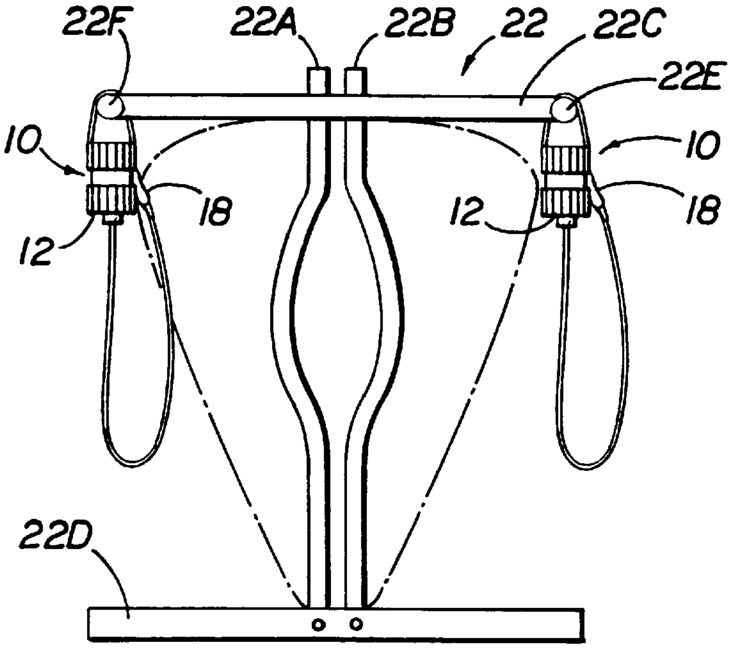
FIG. 3 is a front view of a cattle holder having a cattle holder left head member and a cattle holder right head member pivotally attached on a bottom to a cattle holder bottom cross member.

Referring to FIG. 3 which is a front view of a cattle holder (22) having a cattle holder left head member (22A) and a cattle holder right head member (22B) pivotally attached on a bottom to a cattle holder bottom cross member (22D). The animals head is inserted between the cattle holder left head member (22A) and a cattle holder right head member (22B) to secure the animal in place during vaccination. At one distal end of a cattle holder top cross member (22C) is the cattle holder right longitudinal member (22E) securely affixed thereto and at an opposite distal end of the cattle holder top cross member (22C) is a cattle holder left longitudinal member (22F) securely affixed thereto. Preferably, the vaccine pack (10) is removably fastened circumferentially around, by the strap (14), either or both the cattle holder right longitudinal member (22E) and/or the cattle holder left longitudinal member (22F). The versatility of easily removably attaching the vaccine pack (10) by the strap (14) allows one user on one side of the animal and another user on another side of an animal for simultaneous administration of vaccine.

Figure 4:
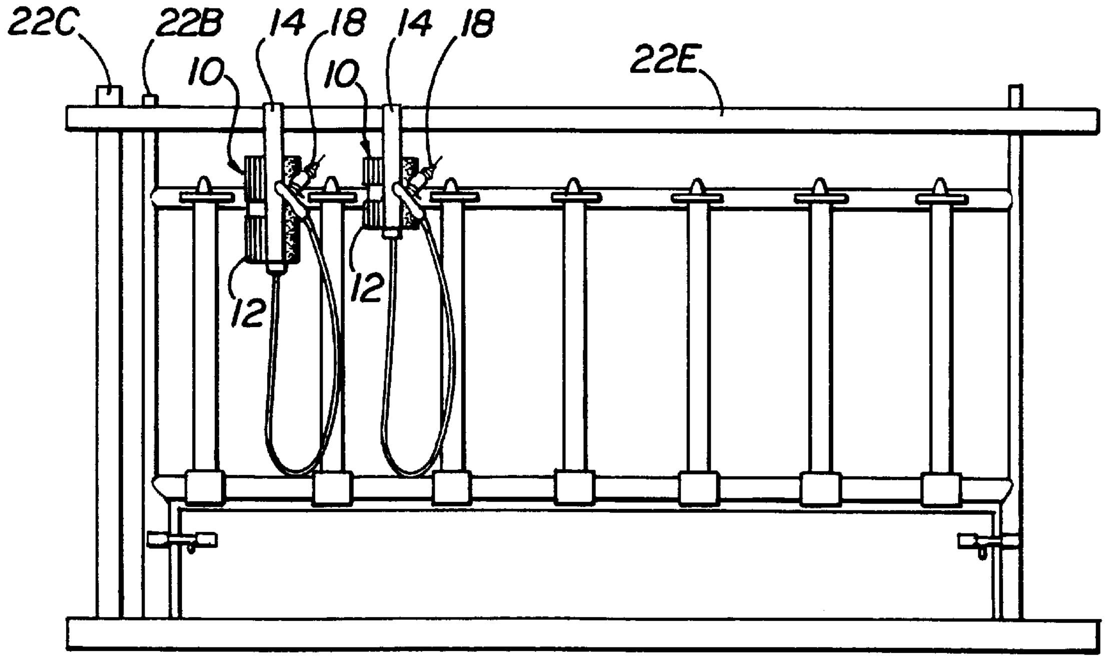
FIG. 4 is a side view of a cattle holder exhibiting a cattle holder right longitudinal member which is attached to a cattle holder top cross member, the cattle holder right longitudinal member has two different sized vaccine packs each attached to the cattle holder right longitudinal member by a separate strap.

Lastly, referring to FIG. 4 which is a side view of a cattle holder (22) exhibiting a cattle holder right longitudinal member (22E) which is attached to a cattle holder top cross member (22C), the cattle holder right longitudinal member (22E) has two different sized vaccine packs (10) each attached to the cattle holder right longitudinal member (22E) by a separate strap (14). The vaccine packs (10) are preferably manufactured in different sizes corresponding to a type of vaccine and dosage being utilized. Some vaccines require twice the dosage of another vaccine and if both vaccine were being utilized simultaneously from the same sized container, the users would have to change one of the vaccines and hence, one of the vaccine packs (10) twice as often as the other vaccine if different sized vaccine packs (10) were not utilized.

It will be understood that each of the elements described above, or two or more together, may also find a useful application in other types of constructions differing from the type described above.

While the invention has been illustrated and described as embodied in a vaccine pack, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. A vaccine pack comprising:

A) a container which comprises a container exterior, a container interior, a container top, and a container bottom having a container bottom opening therein;

B) a strap which comprises a strap first fastener securely mounted on one distal end, the strap is securely fastened to the container exterior at an opposite distal end, the container exterior having a strap second fastener securely mounted thereon, the strap second fastener functioning to removably attach the strap first fastener thereon when the strap is circumventially positioned around a secure member; and C) an automatic syringe which comprises an automatic syringe vaccine inlet positioned through the container bottom opening and securely fastened to the container bottom, the automatic syringe vaccine inlet waterproofly connected to a first distal end of an automatic syringe hose which is waterproofly connected to an automatic syringe vertical handle at an opposite distal end, the automatic syringe horizontal handle having an automatic syringe trigger for actuating the syringe, an automatic syringe needle fastener is fastened to a distal end of the automatic syringe horizontal handle by an automatic syringe needle fastener horizontal handle fastener positioned at an inner distal end which is slightly larger in diameter than a diameter of the automatic syringe horizontal handle, a needle, the automatic syringe needle fastener functioning to receive the needle in an automatic syringe needle fastener opening positioned at an outer distal end.

2. The vaccine pack as described in claim 1, wherein the container exterior further comprises a plurality of needle holders having corresponding needle holder openings securely mounted thereon.

3. The vaccine pack as described in claim 2, wherein the needle holders are manufactured from an elastic strap material.

4. The vaccine pack as described in claim 1, wherein the strap further comprises a label securely fastened thereon.

5. The vaccine pack as described in claim 4, wherein the label has indicia printed thereon, the indicia being selected from a group of indicia consisting of vaccine dosage, type of vaccine, vaccine administration procedure and side effects of vaccine.

6. The vaccine pack as described in claim 1, wherein the automatic syringe horizontal handle further comprises an automatic syringe first fastener securely mounted thereon and the container exterior having a complimentary automatic syringe second fastener securely mounted thereon, the automatic syringe first fastener functioning to allow the automatic syringe horizontal handle to be easily and rapidly removably attached to the container.

7. The vaccine pack as described in claim 6, wherein the automatic syringe first fastener and the complimentary automatic syringe second fastener are hook and loop.

8. The vaccine pack as described in claim 1, wherein the container is constructed from a group of materials consisting of open cell foam, closed cell foam, rubber, rubber composites, plastic, and plastic composites.

9. The vaccine pack as described in claim 1, wherein the strap first fastener and the strap second fastener are hook and loop.

* * * * *